United States Patent [19]
Torck et al.

[11] 4,267,393
[45] May 12, 1981

[54] PROCESS FOR PRODUCING ETHERS BY REACTING OLEFINS WITH ALCOHOLS

[75] Inventors: Bernard Torck, Boulogne sur Seine; Hugo Van Landeghem, Oytier Saint Oblas; Quang D. Vu, Paris; Michel Hellin, Andresy, all of France

[73] Assignee: Institut Francais du Petrole, Rueil-Malmaison, France

[21] Appl. No.: 92,317

[22] Filed: Nov. 8, 1979

[30] Foreign Application Priority Data

Nov. 8, 1978 [FR] France ................................ 78 31768

[51] Int. Cl.$^3$ ............................................ C07C 41/06
[52] U.S. Cl. .................................................... 568/697
[58] Field of Search ......................................... 568/647

[56] References Cited

FOREIGN PATENT DOCUMENTS 929537 7/1973 Canada ..................................... 568/697

*Primary Examiner*—Howard T. Mars
*Attorney, Agent, or Firm*—Millen & White

[57] ABSTRACT

An ether is prepared by reacting a selected olefin with an alcohol in a two reaction zone system: in the first reaction zone, the catalyst is dispersed in the liquid phase of the reactants and boiling of the mixture is avoided; in the second reaction zone, the catalyst is in a fixed bed. A cooled recycle stream is fed back to the first stage reactor. The catalyst is a sulfonated ion exchange resin in the acid form.

18 Claims, 1 Drawing Figure

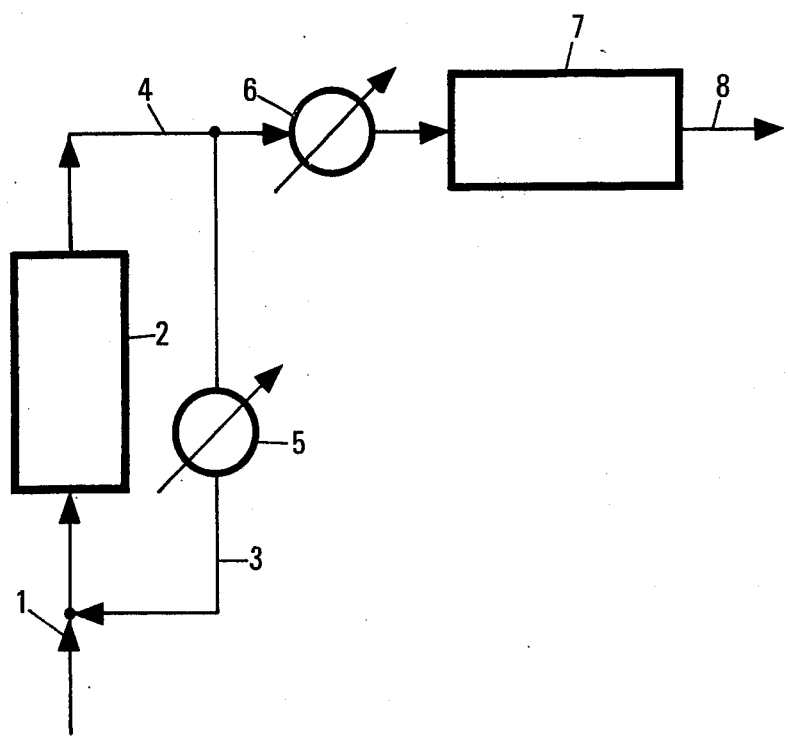

PROCESS FOR PRODUCING ETHERS BY REACTING OLEFINS WITH ALCOHOLS

BACKGROUND OF THE INVENTION

This invention relates to the production of ethers by reacting at least one alcohol with at least one mono-olefin having a double bond on a tertiary carbon atom.

This reaction is known to take place in the presence of acid catalysts, particularly solid ion exchange resins in the acid form, the best results being obtained by using macroreticular solid sulfonic resins, for example those disclosed in U.S. Pat. No. 3,037,052.

The alcohol is, for example, methanol or ethanol and the mono-olefin has a double bond on a tertiary carbon atom as, for example, isobutene, 2-methyl-1-butene, 2-methyl-2-butene, 2-methyl-1-pentene or 2-methyl-2-pentene. Mixtures of olefins may be used. The olefins of the above type, for example isobutene, are more reactive than the bi-secondary olefins, for example 2-butene, or the primary-secondary olefins, for example 1-butene, so that it is possible to treat mixtures of olefins. The olefins having a tertiary carbon atom react nearly exclusively, which is a way to eliminate these olefins from a hydrocarbon stream, for example, a $C_4$ steam-cracking or catalytic cracking cut which may contain butadiene and/or saturated hydrocarbons.

The reaction of adding alcohols to olefins, which yields ethers, is a balanced and exothermic reaction.

It is thus necessary to eliminate the reaction heat, since the sulfonic resins do not withstand temperatures higher than 120° C. over extended periods, and sudden heat thrusts are detrimental to the physical behaviour of the resin. It is also clear that high conversion rates are more easily attained when operating at a low temperature; however, the activity of the resin becomes a limiting factor.

Various techniques have been proposed to optimize this reaction of adding alcohols to olefins. It is thus known, for example, to pass the reactants in the liquid state through the particles of catalyst in fixed bed. It is found that, for reasons of physical behaviour of the resin and to avoid too high irreversible pressure drops due to the piling of the resin, it is desirable to arrange the catalyst as a number of low height catalyst layers and to cool the liquid when passing from a given layer to the next one. Another way to operate with a fixed bed is to pass the liquid through a number of externally cooled parallel tubes containing the catalyst. However, in that case, the reactor is complex and expensive, and it is difficult to avoid unequal distribution of the liquid flow through the tubes, resulting in unsatisfactory running of the reactor and accelerated decay of the resin.

The use of a reactor containing a catalyst dispersed throughout the liquid phase of the reactants does not provide for high olefin conversion rates, unless reactors of excessive volume are used.

It has also been proposed to operate in two serially arranged reactors with intermediary separation of the product or to use molar alcohol/olefin ratios higher than 1, in order to obtain increased conversion rates. In all these cases, the power necessary to distill either the hydrocarbon cut, for example a $C_4$ cut, or methanol or other alcohol in excess to be recycled, is considerably increased.

It has also been proposed to operate with two successive catalyst beds (Patent application of the German Federal Republic No. 1,934,422). In the first bed, the catalyst is maintained dispersed in the liquid by the vaporization of one or more constituents of the liquid to dissipate a part of the reaction heat. The second bed consists of the catalyst accumulated in the bottom of the reactor. The temperature conditions are thus the same for the first bed and the second bed of the catalyst. The liquid is circulated downwardly.

It has been found that this technique has a great disadvantage: the vapor phase appears within the resin particle or at the contact surface thereof and forms an envelop therearound, thus impeding an easy access of the reactants, which leads to relatively poor conversions and selectivities and a reduced life of the catalyst. Another disadvantage is that the compound of lowest boiling point, the olefin in most cases, vaporizes and escapes from the reaction or, at the least, undesirably modifies the proportions of the reactants.

OBJECTS OF THE INVENTION

It has been found that, when reacting an alcohol with an olefin to form an ether, higher yields, less secondary reactions and lengthened life of the resin are obtained when operating according to a process based on concepts different from the foregoing, viz:
  operate with at least one bed of dispersed catalyst followed with at least one bed of fixed catalyst, while using a different system for dispersing the catalyst,
  operate with a dispersed catalyst, but avoid the vaporization of the liquid when contacted with the particles of catalyst,
  operate with a dispersed catalyst, but remove the heat by another way than vaporization,
  complete the reaction by contact with a fixed bed catalyst, while operating at a temperature substantially lower than measured at the outlet from the contact zone with the dispersed catalyst.

SUMMARY OF THE INVENTION

These objects are attained when operating as follows:

A liquid mixture of the reactants, alcohol and olefin, with a recycle stream is passed upwardly in a reaction zone (A) containing a bed of solid catalyst particles of the sulfonated ion exchange resin type in the acid form, at a temperature of 60°–120° C., preferably 80°–100° C. for a $C_4$ cut and 70°–90° C. for a $C_5$ cut, selected lower than the boiling temperature of the most volatile and constituent of the mixture, under the selected pressure, a feed rate of the mixture sufficient to expand the volume of said bed by at least 2% is maintained, said feed rate being insufficient to carry the catalyst substantially out of said zone (A), while selecting the contact time so as to convert 60–95% of the reactant olefin, the resultant liquid mixture is discharged, a portion thereof is cooled and then recycled and a second portion is fed to a second reaction zone (B) containing a fixed bed of solid catalyst of the same type, at a temperature of 30°–70° C., preferably 45°–60° C., lower by at least 10° C. than the temperature measured at the outlet from the reaction zone (A) and itself selected lower than the boiling temperature of the constituent of highest volatility, under the selected pressure.

DETAILED DISCUSSION

The process may be conducted in adiabatic reactors of simple design and low cost. The reaction heat evolved in the first reaction zone may be used in part to heat the reactants charge and the remainder may be evolved outside of the reaction zone by passing the effluent through a conventional heat exchanger before recycle to the inlet of said zone. The stirring of the catalyst in the first reactor avoids the disadvantages linked to an increase of the pressure drop and avoids heat shocks in the resin, due to better and more homogeneous temperature distribution. The re-circulation of the effluent, which is cooled in an external exchanger, results in better control of the temperature gradients and concentrations in the reaction zone and makes it possible to operate with the resin at a higher temperature. It is found that these particular conditions of operation lead, in spite of increased temperature in the first reaction zone, to higher selectivities for tertiary ethers, e.g., methyl t-butyl ether (MtBE) and an increased life of the resin.

The circulation rate of the liquid mixture in the first reaction zone depends on the size and the density of the particles of catalyst. In most of cases, this rate is from 0.5 to 10 cm/sec., preferably 1 to 4 cm/sec.

The size of the catalyst particles is usually from 0.05 to 5 mm, preferably from 0.3 to 1.5 mm when the circulation rate is 1 to 4 cm/sec.

The recycle rate is usually 0.1 to 15 times, preferably 0.5 to 4 times the feed rate of the fresh charge of the reactants. The latter is usually 0.5 to 20 liquid volumes per volume of the reactor containing the catalyst and per hour (hourly space velocity).

A detailed description of the catalyst is given, for example, in U.S. Pat. No. 3,037,052.

The pressure in the first and second reaction zones must be sufficient to maintain the reactants in liquid phase at a temperature above the boiling point of the most volatile constituent of the charge. Under this condition, the pressure is usually from 5 to 50 bars.

The conversion of the reactant olefin is selected from 60 to 95%, preferably from 75 to 92% for the first reaction zone in the case of isobutene and 40 to 75%, preferably 50 to 70% in the case of the 2-methyl 1- and 2-butenes.

In the second reaction zone, the catalyst may be selected with the same particle size as defined for the first reaction zone. The conversion of the reactive olefin is preferably such as to have a total conversion of at least 90% with at least 3% in the second reaction zone in the case of isobutene, and at least 70% with at least 3% in the second reaction zone in the case of the 2-methyl 1- and 2-butenes.

It is also noted that the composition of the feed charge to the second reaction zone is preferably essentially the same as that of the effluent from the first reaction zone.

The invention is illustrated by reference to drawing.

The mixture of the reactants, alcohol and olefin, is fed through duct 1 to reactor 2 after having been admixed with the recycle stream (line 3). The reactor contains a catalyst of appropriate size, for example Amberlyst 15. The velocity is such as to suspend the catalyst, although not to carry it away from the reactor. The effluent (line 4) is divided to a recycle stream 3 passing through exchanger 5 and a product stream passing through exchanger 6 and then through the reactor 7 containing a fixed bed of catalyst. The product of the reaction is collected in pipe 8.

Instead of the two exchangers 5 and 6, only one exchanger can be used, which is arranged on duct 4 before separation between the recycle stream and the stream supplied to reactor 7.

In examples 2 and 4, the temperature is maintained below the boiling temperature.

EXAMPLE 1

This example illustrates the use of the known process with a fixed bed catalyst.

A $C_4$ steam-cracking cut having the following composition:

Isobutene 48% by weight
1-butene 25.5% by weight
cis 2-butene 4.6% by weight
trans 2-butene 10.5% by weight
butadiene 0.4% by weight
other $C_4$ hydrocarbons 11% by weight is admixed with methanol to have a methanol/isobutene molar ratio of 1.08 and the whole is supplied in the liquid state to a reactor containing the Amberlyst 15 sulfonic resin (grain size: 0.4 to 1 mm) arranged in fixed bed, at an hourly space velocity (volume of liquid per volume of catalyst per hour) of 4. The reactor pressure is maintained at 20 atmospheres. The temperature of the reaction is controlled with water circulated in an external jacket. The effluent temperature is 60° C. The results of the Table show, versus time, that the conversion rate of isobutene to MtBE decreases and that the contents of the effluent in isobutene dimers and isobutene-n-butenes codimers, in methyl ether derived from the n-butenes and in tertiary butyl alcohol are relatively high.

| Time in hours | 50 | 200 | 2000 |
|---|---|---|---|
| Rate of conversion, isobutene | 0.95 | 0.94 | 0.90 |
| % MtBE by weight | 53.2 | 52.7 | 50.7 |
| % dimers and codimers by weight | 3.5 | 3.3 | 3.0 |
| % methyl sec . butyl ether by weight | 1.0 | 1.0 | 0.9 |
| % t . butyl alcohol by weight | 0.8 | 0.8 | 0.7 |

EXAMPLE 2

This example illustrates the process of the invention. The conditions are so selected as to have substantially the same conversion rate of isobutene as in example 1.

A steam-cracking $C_4$ cut having the same composition as in example 1 is admixed with methanol, so that the molar ratio methanol/isobutene is 1.08 . This mixture of the reactants is supplied to the bottom of a first reactor arranged vertically and containing the sulfonic resin Amberlyst 15 of same particle size as in example 1. A portion of the effluent from the first reactor is added to the mixture of the reactants, so that the aggregate linear velocity is 2 cm/sec. The effluent recycle rate is 1.0. The expansion rate is 25%. The recycled effluent is cooled in an external exchanger, so that the reaction is adiabatic. Temperature: 78° C. (inlet) and 90° (outlet). The reaction is effected in liquid phase while maintaining the reactor pressure at 20 atmospheres. The hourly liquid space velocity is 5.5 in the first reactor and the conversion of isobutene is 84%. The outflow is then cooled to 50° C. and fed to a second reactor, at a space velocity of 3, where the reaction is also adiabatic. The outlet temperature is 60° C.

The results are given in the following table.

| Time in hours | 50 | 200 | 2000 |
|---|---|---|---|
| Rate of conversion, isobutene | 0.95 | 0.95 | 0.93 |
| % MtBE by weight | 55.4 | 55.4 | 54.2 |
| % dimers and codimers by weight | 0.8 | 0.8 | 0.75 |
| % methyl sec . butyl ether by weight | 0.5 | 0.5 | 0.45 |
| % t . butyl alcohol by weight | 0.3 | 0.3 | 0.3 |

A comparison with the results of example 1 shows that, when operating according to the process of this invention, the stability of the catalyst is better and the selectivity for MtBE is higher

EXAMPLE 3

This comparison example illustrates the known process in which the dispersion of the catalyst and the heat removal, in the first reactor, result from the boiling to reflux of the reaction mixture.

A test is effected in the same conditions as in example 2, but the pressure in the reactor is 11 atmospheres, instead of 20, the average temperature (84° C.) is the same and the outflow is supplied directly to the second reactor, without recycling of a portion thereof to the first reactor, thus without cooling outside of the first reactor.

The results are given in the following table:

| Time in hours | 50 | 200 | 2000 |
|---|---|---|---|
| Rate of conversion, isobutene | 0.85 | 0.84 | 0.81 |
| % MtBE by weight | 46.3 | 45.2 | 43.5 |
| % dimers and codimers by weight | 1.5 | 2.5 | 2.5 |
| % methyl sec . butyl ether by weight | 1.3 | 1.4 | 1.3 |
| % t . butyl alcohol by weight | 0.5 | 0.5 | 0.5 |

The results show that the production of MtBE is lower and the formation of the by-products greater.

EXAMPLE 4

A steam-cracking $C_5$ cut having the following composition:
- 2-methyl-1-butene: 5.4% by weight
- 2-methyl-2-butene: 27.1% by weight
- other $C_5$ olefins: 35.9% by weight
- $C_5$ saturated hydrocarbons: 31.6% by weight is admixed with methanol, so that the molar ratio methanol/2-methyl-1-butene+2-methyl-2-butene is 1.3, and the whole is supplied in the liquid state into a reactor containing Duolite C 26 resin (particle size from 0.5 to 1.2 mm). A part of the outflow from this first reactor is added to the mixture of the reactants, so that the linear velocity is 2 cm/second. The recycle rate of the outflow is 3, and the expansion rate is 23%. The recycled outflow is cooled in an external exchanger, so that the reaction is substantially adiabatic and the temperature is 68° C. at the inlet and 75° C. at the outlet. The reaction is effected in liquid phase while maintaining the reactor pressure at 8 atmospheres. The liquid space velocity is 2.1 in the first reactor. The effluent is then cooled to 52° C. and fed at an hourly liquid space velocity of 3, to a second reactor where the reaction is also substantially adiabatic. The outlet temperature is 60° C.

The results are given in the following table:

| Time in hours | 50 | 200 | 2000 |
|---|---|---|---|
| Rate of conversion methylbutenes | 0.73 | 0.73 | 0.72 |
| % b.w. t . amyl methyl ether | 28.5 | 28.5 | 28.1 |
| % b.w. dimers and codimers | 0.2 | 0.2 | 0.15 |
| % b.w. methyl sec . pentyl ether | 0.3 | 0.3 | 0.3 |
| % b.w. t . amyl alcohol | 0.2 | 0.2 | 0.2 |

EXAMPLE 5

By way of comparison, the reaction is effected with the same $C_5$ cut and the same operating conditions as in the preceding example, except that the pressure is now 3 atmospheres, and without recycling of a part of the reactor outflow.

In this example the reaction heat was removed by boiling to reflux. After 50 hours of run, the following results are obtained:

| Time in hours | 50 |
|---|---|
| Rate of conversion methylbutenes | 0.60 |
| % b.w. t . amyl methyl ether | 21.0 |
| % b.w. dimers and codimers | 2.0 |
| % b.w. methyl sec . pentyl ether | 1.8 |
| % b.w. t . amyl alcohol | 0.5 |

What is claimed is:

1. In a process for manufacturing ethers by contacting a mixture of at least one olefin having a double bond on a tertiary carbon atom and at least one alcohol with a sulfonated ion exchange resin catalyst in the acid form, the improvement comprising passing a liquid mixture of fresh reactants comprising said at least one olefin and said at least one alcohol, together with a liquid recycle stream as hereinafter defined at a feed rate of from 0.1 to 15 times the feed rate of the fresh reactants, upwardly through a first reaction zone containing a catalyst bed of particles of said sulfonated ion exchange resin in the acid form, at a temperature of from 60° to 120° C., said temperature being lower than the boiling temperature of the constituent of highest volatility in the mixture passing through the first reaction zone at the selected pressure, while maintaining a feed rate which is sufficient to expand the volume of said catalyst bed by at least 2% and to disperse the catalyst particles therein but insufficient to carry a substantial proportion of catalyst out of said first reaction zone, the contact time being selected to convert from 60 to 95% of said olefin; discharging the liquid product mixture formed in the first reaction zone, cooling a first portion thereof, and recycling the cooled portion to the first reaction zone as said liquid recycle stream, and feeding a second portion of said liquid product mixture to a second reaction zone containing a fixed bed of said sulfonated ion exchange resin catalyst in the acid form, at a temperature of from 30° to 70° C., the temperature in the second zone being at least 10° C. lower than the outlet temperature of the first reaction zone and lower than the boiling temperature of the constituent of highest volatility in the mixture passing through the second reaction zone at the selected pressure.

2. A process according to claim 1, wherein substantially adiabatic conditions are maintained in said first reaction zone, and at least the major part of the reaction heat evolved in the first reaction zone is extracted from the recycle stream outside of said first reaction zone.

3. A process according to claim 2, wherein the circulation rate of the liquid mixture of reactants in the first reaction zone is from 0.5 to 10 cm/sec and the size of the catalyst particles is from 0.05 to 5 mm.

4. A process according to claim 3, wherein the circulation rate of the liquid mixture of the reactants is from 1 to 4 cm/sec and the size of the catalyst particles is from 0.3 to 1.5 mm.

5. A process according to claim 1, wherein the recycle rate is 0.5 to 4 times the feed rate of the fresh charge of reactants.

6. A process according to claim 1, wherein the olefin is isobutene and its total conversion is at least 90%, with at least 3% in the second reaction zone.

7. A process according to claim 6, wherein the alcohol is methanol.

8. A process according to claim 6, wherein isobutene is supplied as a steam-cracking or catalytic cracking $C_4$ cut.

9. A process according to claim 8, wherein the $C_4$ cut also contains butadiene.

10. A process according to claim 1, wherein said at least one alcohol is at least one alkanol.

11. A process according to claim 1, wherein said at least one alcohol is at least one of methanol and ethanol.

12. A process according to claim 1, wherein the temperature in the second reaction zone is from 45° to 60° C.

13. A process according to claim 1, wherein the pressure in the first and second reaction zones is from 5 to 50 bars.

14. A process according to claim 6, wherein the temperature in the first reaction zone is from 80° to 100° C., and the conversion of isobutene in the first reaction zone is from 75 to 92%.

15. A process according to claim 1, wherein the olefin is at least one of 2-methyl-1-butene and 2-methyl-2-butene and its total conversion is at least 70%, with at least 3% in the second reaction zone.

16. A process according to claim 15, wherein the alcohol is methanol.

17. A process according to claim 15, wherein said at least one of 2-methyl-1-butene and 2-methyl-2-butene is supplied as a steam cracking or catalytic cracking $C_5$ cut.

18. A process according to claim 15, wherein the temperature in the first reaction zone is from 70° to 90° C., and the conversion in the first reaction zone is from 50 to 70%.

* * * * *